(12) United States Patent
Kunji et al.

(10) Patent No.: US 8,507,262 B2
(45) Date of Patent: Aug. 13, 2013

(54) APPARATUS AND METHOD FOR MONITORING CULTURES

(75) Inventors: Edmund Kunji, Cambridge (GB); Shane Palmer, Cambridge (GB)

(73) Assignee: Cytoprom Ltd, Cambridge (GB)

( * ) Notice: Subject to any disclaimer, the term of this patent is extended or adjusted under 35 U.S.C. 154(b) by 1224 days.

(21) Appl. No.: 12/161,389

(22) PCT Filed: Feb. 23, 2007

(86) PCT No.: PCT/GB2007/000618
§ 371 (c)(1),
(2), (4) Date: Oct. 23, 2008

(87) PCT Pub. No.: WO2007/096626
PCT Pub. Date: Aug. 30, 2007

(65) Prior Publication Data
US 2010/0233751 A1    Sep. 16, 2010

(30) Foreign Application Priority Data
Feb. 23, 2006  (GB) .................................. 0603589.3

(51) Int. Cl.
*C12Q 1/02* (2006.01)
*C12M 1/34* (2006.01)
*B23P 11/00* (2006.01)

(52) U.S. Cl.
USPC ......... 435/288.7; 435/287.1; 435/29; 29/428; 422/68.1; 422/81; 422/98; 436/52; 436/68; 436/150

(58) Field of Classification Search
USPC ...... 435/288.7, 29, 287.1; 29/428; 422/68.1, 422/81, 98; 436/52, 68, 150
See application file for complete search history.

(56) References Cited

U.S. PATENT DOCUMENTS

| | | | | |
|---|---|---|---|---|
| 3,560,099 A * | 2/1971 | Boe et al. | ....................... | 356/246 |
| 3,849,002 A * | 11/1974 | Hach | ............................. | 356/339 |
| 4,361,539 A * | 11/1982 | Weinberg et al. | .......... | 422/82.02 |
| 4,361,540 A * | 11/1982 | Weinberg et al. | .......... | 422/82.02 |
| 4,398,930 A | 8/1983 | Larson | | |
| 4,443,407 A * | 4/1984 | Weinberg et al. | .......... | 422/82.04 |
| 4,595,561 A | 6/1986 | Thornton | | |
| 4,725,148 A * | 2/1988 | Endo et al. | .................... | 356/442 |
| 5,335,067 A * | 8/1994 | Prather et al. | ................. | 356/436 |
| 5,831,727 A * | 11/1998 | Stream | .......................... | 356/246 |

FOREIGN PATENT DOCUMENTS

EP         0810281 A2      12/1992

* cited by examiner

*Primary Examiner* — William H Beisner
*Assistant Examiner* — Danielle Henkel

(57) ABSTRACT

Disclosed is a bubble excluder device (2) adapted for use with, and attachment to, a probe (6) for continuous measurement of the cell density of a culture in a liquid medium; the bubble excluder device comprising an inlet and an outlet to allow flow of liquid through the device and bubble exclusion means (20) to reduce or prevent ingress of bubbles from the liquid medium outside the device.

18 Claims, 6 Drawing Sheets

APPARATUS AND METHOD FOR MONITORING CULTURES

FIELD OF THE INVENTION

The present invention relates to apparatus for, and a method of, continuous monitoring of the cell density of a cell culture within an aerated fermenter.

BACKGROUND OF THE INVENTION

The process of aerobic fermentation provides an important mechanism for the formation of certain products, such as enzymes, antibiotics, diagnostics and therapeutics. Such products are typically produced by the overexpression of a protein in cells of a microorganism, such as *E. coli* or *S. cerevisiae*.

On a laboratory scale, such substances of interest are typically produced by preparing a "starter" culture which is then used to inoculate a larger volume of culture medium. Typically, the culture medium is contained within a conical flask and is placed in an incubator at a desired temperature. The growth of cells in the culture medium is monitored by intermittent sampling of small amounts of the culture and measurements of the optical density of the culture medium with the use of an external spectrophotometer. By way of explanation, measuring the optical density at approximately 600 nm detects scattering of light by microorganisms and the resulting OD reading is proportional to the cell density. The cells grow and divide and, typically, when the optical density of the culture has reached a desired value, the overexpression of a protein of interest is induced, for example, by a change in temperature or the addition of an inducer, etc.

Aerobic fermentation is routinely carried out on an industrial scale in stirred tanks. Typically, an optical probe is used to measure the optical density of the culture medium according to the Beer Lambert Law, which is defined by the following equation:

$$OD = E.L. \log_{10}(I_o/I)$$

wherein
E=Extinction coefficient;
L=Path length of cell;
$I_o$=Incident light intensity;
I=transmitted light intensity In industrial-scale fermentations, vigorous agitation and aeration is normally required in order to support optimal growth of the microorganisms or cells because they need to respire. Under such conditions, as much as a fifth of the overall aerated liquid volume of the culture medium may comprise gas bubbles dispersed in the liquid. Good liquid mixing of aerated medium means that many of these gas bubbles are small enough to pass through the light path of the optical probe used to measure the cell density of the culture. The presence of gas bubbles in the culture medium may have an effect on the apparent cell density of the medium, because gas bubbles have different light-scattering properties compared to the culture medium and the cells that are suspended therein. Scattering of light by bubbles in the medium tends to cause an overestimation of the apparent optical density of the medium. In particular, at low cell densities (where the gas bubble to cell ratio is greatest), the random nature of the size and concentration of the gas bubbles at the point of measurement in the stirred tank results in 'noise', which is shown as data scatter in the cell density measurements. For certain applications, such as fluorescence tagging, this is a problem as in such cases it is necessary to detect very small changes in absorbance, at values beyond the standard level of precision. In addition, the rate of aeration and agitation may vary during fermentation, such that the effect of bubbles on the measurements made is also variable.

Although other methods may be used to monitor the growth of microorganisms during aerobic fermentation (such as measurement of carbon dioxide production rate, oxygen consumption rate or fluorescence), the preferred method involves measurement of the cell density of a culture because it is less sensitive to culture conditions, such as temperature and pH. In most cases, the measurement of the culture's optical density is carried out 'off-line' using a spectrophotometer, typically in the region of 600 nm. By way of explanation, 'off-line' measurement of the optical density of a culture involves removing a sample of medium and measuring the optical density of the sample using an external spectrophotometer. However, such 'off-line' measurement typically has the disadvantages that it may increase the time, cost, and loss of culture volume and also increases the risk of contamination of the fermenter. In addition, using conventional methods, the cell density of a culture may only be directly measured accurately for values below 0.8, preferably below 0.7 optical density (OD) units. This is due to the fact that above these values the relationship between the cell density and optical density is no longer linear. In order to measure OD values above 0.7-0.8, the samples must be diluted and the resulting measurements multiplied by a dilution factor, such that the OD value does not exceed 0.8 units and preferably does not exceed 0.7 units. However, such dilution may introduce errors in the determination of cell density and renders on-line measurements of OD impossible.

By way of explanation, the 'on-line' measurement of the optical density of a culture involves the use of an in situ probe immersed in a culture medium to monitor changes in the cell density of a culture during fermentation. However, such methods have the added complication that air bubbles must be removed from the culture medium prior to measurement, in order to produce an accurate and reliable determination of the optical density. Thus, such methods typically require the addition of a separate device to degas the medium and consequently do not provide a method for a continuous measurement of the optical density of the medium.

The use of an on-line probe for monitoring concentration changes in a culture is known in the art. Shiloach and Bahar (Sixth European Congress on Biotechnology, Florence, Italy, 1993) disclose the use of a sterilisable, on-line sensor (Cerex Corporation) that is capable of following changes in culture turbidity. The probe is based on light emission from a culture and provides a good correlation to off-line turbidity measurements. The probe can be interfaced to a data acquisition and control system such that it can provide direct measurements during the fermentation process. During operation of the probe, a teflon plunger with an embedded magnet moves up and down as a result of an alternating magnetic field. The plunger movement allows culture medium to flow into a sampling chamber provided within the probe and facilitates removal of air bubbles from the culture medium. Typically, the plunger movement cycles such that it is open for one minute and closed for one minute providing a new optical density value every two minutes. Thus, although the on-line sensor overcomes the requirement associated with off-line systems wherein a sample of culture medium is removed from the fermenter in order to measure the optical density externally using a spectrophotometer, the probe disclosed by Shiloach and Bahar does not allow continuous measurement of the optical density.

Combs and Bishop (Annual Meeting of the Society for Industrial Microbiology, Toronto, Canada, 1993) disclose the use of a similar on-line probe (Cerex Corporation) to measure the optical density of a culture during fermentation. During operation of the probe, a solenoid opens, culture medium enters the sampling chamber, a valve closes to de-bubble the culture through a riser port and the optical density of the sample is measured. Thus, the operation of the probe requires the opening and closing of a valve, such that the on-line measurement of the optical density of the medium is not continuous.

SUMMARY OF THE INVENTION

In a first aspect the invention provides a bubble excluder device adapted for use with, and attachment to, a probe for continuous measurement of the cell density of a culture in a liquid medium; the bubble excluder device comprising an inlet and an outlet to allow flow of liquid through the device; and bubble exclusion means to reduce or prevent the ingress of bubbles from the liquid medium outside the device.

Conveniently the device will comprise a sleeve which fits around the probe, the inlet and outlet allowing the liquid medium to communicate with the probe and, more especially, with a sampling aperture of the probe. The inlet and the outlet may be provided with a shared or common channel in the device or, more preferably, may be discrete components at different locations on the device.

The bubble exclusion means may comprise, for example, a one-way valve or other flow restriction mechanism. Preferably the bubble exclusion means comprises a plurality of baffles, or perforated plates, or other mechanism of forcing a serpentine flow path. The bubble exclusion means may conveniently be located in the inlet and/or the outlet of the bubble excluder device. The bubble exclusion means may act to exclude bubbles on the basis of size, or the relative buoyancy of bubbles (relative to the liquid of the culture medium), or both size and buoyancy. In one preferred embodiment, the device comprises a channel with a cross-sectional area which is smaller than the diameter of the majority of the bubbles in the liquid medium, which will therefore be excluded from the channel.

The bubble excluder device will preferably comprise a conduit, which conduit comprises bubble exclusion means. In a preferred embodiment the bubble exclusion means comprises a structural feature or features which create a serpentine flow path within the conduit. For example, a serpentine flow path within the conduit may be created by a plurality of overlapping baffles or perforated plates.

Each perforated plate may comprise a single or a few relatively large perforations, or may comprise a plurality (say five or more) of relatively small perforations. Where a large number of perforations are provided, each perforation may be fairly small, such that the majority of bubbles present in the liquid medium are unable to pass through the perforated plates (note that, in such an embodiment, there is no requirement for the flow path to be serpentine)—the large number of perforations nevertheless allows for only modest resistance to flow of liquid. Where only one or two perforations are provided in each plate these must necessarily be of relatively large size (e.g. a circular hole of 4-6 mm diameter) in order not to severely restrict flow of liquid, and are preferably positioned towards alternate sides of successive plates, in order to create a serpentine flow path.

The conduit will typically constitute the inlet of the bubble excluder device, but the direction of flow of liquid through the device may vary according to localised conditions within the fermenter, such that the conduit may occasionally act as the liquid outlet, or even simultaneously as an outlet and an inlet.

In a second aspect, the present invention provides a bubble excluder device in accordance with the first aspect of the invention, in combination with a probe for continuous measurement of the cell density of a culture, the probe comprising a sampling aperture exposed to the culture within the bubble excluder device to allow the probe to measure a characteristic of the culture.

In a preferred embodiment, the bubble excluder device/probe combination of the present invention allows the on-line measurement of the cell density of a culture.

In accordance with the present invention, the term 'on-line' refers to a bubble excluder device/probe combination which is in continuous fluid communication with the culture medium. In one embodiment, the bubble excluder device/probe combination is provided in situ, i.e. in the fermenter. In another embodiment, the bubble excluder device/probe combination is provided outside the fermenter, but is in continuous fluid communication with the culture medium by means of, e.g. a pipe, tube or other fluid flow channel.

The term 'off-line' refers to the intermittent measurement of cell density of a culture. The provision of a conduit and an inlet means eliminates the requirement associated with the prior art wherein the culture medium must be degassed prior to measurement of the cell density. Thus, the present invention advantageously allows the continuous measurement of the cell density of a culture throughout fermentation.

Typically, the measurement of the cell density of the culture medium may be made by, either taking a direct reading of the transmittance of the culture or calculating an optical density value.

In accordance with the present invention, the bubble excluder device/probe combination may be used to measure a characteristic of a culture such as resistance or electrical conductivity. Preferably, the characteristic of the culture that is measured is an optical characteristic. More preferably, the characteristic measured is the optical density of a culture, such as the optical density of a culture in the range of 500-700 nm. Most preferably, the characteristic measured is the optical density of a culture which is approximately 600 nm or is the colour or fluorescence of a protein expressed by the cells that are cultivated in the fermenter. However, the measurement of optical density of a culture is not restricted to the range of 500-700 nm and the bubble excluder device/probe combination of the present invention may be used to measure the optical density of a culture across the full waveband of a spectrophotometer, including measurement in the UV range.

Preferably, the probe which may be used in combination with the bubble excluder device of the present invention is an optical probe. More preferably, the probe of the present invention uses fibre optics to measure the optical density of the culture medium at one or more selected wavelengths. Typically, a tube or sleeve is placed around the optical fibres of the optical probe. Most preferably, the optical probe comprises two parallel optical fibres which form a light path and transmit light in opposite directions. In one embodiment, the light path passes through the sampling aperture and is reflected, for example, by means of two prisms provided at the end of the optical probe, such that the direction of the light path is reversed.

In one embodiment, a spectrophotometer is coupled to the optical probe, e.g. by means of optical fibres. The spectrophotometer measures the optical density of the culture medium at a desired wavelength or a range of wavelengths. The probe which may be used in combination with the bubble excluder device of the present invention allows continuous optical density measurements to be made by the spectrophotometer. Direct attachment of the spectrophotometer to the bubble excluder device/probe combination is preferred, as this avoids the requirement for external optical fibres to connect the probe to the spectrophotometer.

Preferably, a sampling aperture is provided within the light path of the optical probe. More preferably, the culture medium is continuously in fluid communication with the sampling aperture in order to allow continuous measurement of the optical density of the culture medium.

In one embodiment, the optical probe uses a 2 mm light path. In a preferred embodiment, the optical probe uses a 1 mm light path. Advantageously, the use of a 1 mm light path facilitates exclusion of gas bubbles from the sampling aperture. The presence of gas bubbles in the culture medium may have an effect on the apparent cell density of the culture medium, because gas bubbles scatter light and displace cells. Thus, the use of a 1 mm light path improves the accuracy of the cell density measurement and allows linear measurement of the growth of a culture at higher cell densities. Generally, a short light path increases the sensitivity of measurements made at higher cell densities.

Conveniently, the bubble excluder device/probe combination of the invention is made by attaching a suitable bubble excluder device to a suitable probe. The probe may be, for example, an otherwise conventional, or substantially conventional, optical probe suitable for measuring cell density, of the sort known in the prior art. Typically, the bubble excluder device/probe combination is made by sliding a sleeve of the bubble excluder device over a probe. Preferably, a channel between the outlet and the inlet of the bubble excluder device is formed such that the channel is substantially in line with the sampling aperture of the probe. More preferably, the dimensions of the bubble excluder device are such that, when connected to the probe, a fluid path is formed which is substantially linear from the inlet of the bubble excluder device, and which fluid path flows across the sampling aperture of the probe. Conveniently, the dimensions of the bubble excluder device are such that, when the probe is positioned as far as possible within the sleeve, this brings about the correct relative positioning of the bubble excluder device and probe. In one embodiment, biased engagement means provided within a channel present in the bubble excluder device are received within a correspondingly shaped and dimensioned recess within the probe when the bubble excluder device and probe are aligned in the correct position. Typically, insertion of the probe compresses a spring provided within the channel of the bubble excluder device. Upon attaining a position wherein the conduit, inlet and sampling aperture are aligned such that the fluid path is substantially linear, the biased engagement means are forced into engagement with the correspondingly shaped and dimensioned recess in the probe.

Preferably, all parts of the bubble excluder device (and preferably of any associated probe) are biocompatible and able to withstand the conditions of sterilisation in place. More preferably, the metal components of the bubble excluder device comprise stainless steel.

Preferably, a sleeve of the bubble excluder is attached to the outer surface of the body of a probe. More preferably, the bubble excluder device attaches to the probe so that in situ the conduit is substantially vertical, such that any gas bubbles (being less dense than the culture medium) will tend to rise up the conduit, away from the sampling aperture. Most preferably, the conduit is attached at a position above sampling aperture of the probe.

In a preferred embodiment, the bubble exclusion means in the conduit comprises a series of overlapping baffles. More preferably, the baffles are provided at an angle such that they slope in an upward direction. The provision of a series of overlapping baffles has the advantage that the upward movement of gas bubbles from the culture medium within the fermenter and through the conduit is relatively unrestricted when compared with the ingress of bubbles from the medium into the interior of the bubble excluder, thus facilitating the removal of gas bubbles from the culture medium within the device, whilst preventing the downward movement of gas bubbles from the external medium. In addition, a relatively calm environment is created within the conduit such that any gas bubbles present within the culture medium are encouraged to move in an upward direction, because gas bubbles have a lower density than culture medium, such that they will rise towards the surface of the culture medium. Thus, physical exclusion, sufficient calming of fluid flow to promote coalescence and the Bernoulli effect all promote the exclusion of gas bubbles from the interior of the bubble excluder device. The Bernoulli effect describes the situation wherein, for horizontal fluid flow, an increase in the velocity of fluid flow results in a reduction in the static pressure of the liquid. Thus, rapid movement of the external culture medium across the top of the conduit generates a suction effect, thus promoting egress of gas bubbles and also facilitating replenishment of the culture medium at the sampling aperture.

The diameter of the conduit is partly determined by typical bubble size distributions found in microbial culture vessels. Preferably, the minimum separation between the overlapping baffles is greater or equal to 4 mm. More preferably, the dimensions of the conduit give a minimum baffle separation of 4.6 mm. Therefore, the internal diameter of a cylindrical conduit should be at least 12 mm to allow a minimum clearance of 4 mm for the bubbles as they rise through the conduit.

In testing, the number of baffles required was the subject of much work. The only limit to the maximum number of baffles is the delay time to the first reading. The delay time is equivalent to the internal volume of the probe divided by the flow rate through the probe. In practice it is not usually important to measure the cell density within the first minute or so of commencing a fermentation, so delay times of this order of magnitude are generally acceptable.

Conveniently the conduit comprises 4-10 baffles, preferably 4-8 baffles, most preferably 4-6 baffles. The baffles are preferably arranged to overlap, so as to create a sinuous or serpentine fluid flow path within the conduit. Preferably the baffles are generally elliptical in shape, with a width substantially equivalent to the internal diameter of the tubing. In one preferred embodiment, the conduit is essentially cylindrical with a circular cross-section, and each of the one or more of the baffles extend across between 55 and 75% of the internal diameter of the conduit. In one preferred embodiment, the baffles are positioned at 45° to the walls of the conduit.

In accordance with the present invention, a fluid tight seal is preferably provided between the sleeve of the bubble excluder device and the outer surface of a probe. The provision of a fluid tight seal is important in regulating the flow of fluids within the bubble excluder device and prevents the entrance of gas bubbles from the external medium into the probe by unregulated means. In a preferred embodiment, the fluid tight seal is provided by means of a silicone or rubber O-ring, a jubilee clip, or by a metal weld or the like.

The outlet of the bubble excluder device may typically be provided as a non-water-tight seal or a self-contained integral feature.

As noted previously, whilst generally the flow of liquid through the bubble excluder device will be from top to bottom, the direction of flow could be reversed depending on the precise localised conditions around the device in the fermenter. Accordingly, the "outlet" may actually function as the inlet on occasion.

Preferably, in use, the outlet is provided on the underside of the bubble excluder device. More preferably, the outlet is substantially aligned vertically with the conduit. Most preferably, the outlet is substantially aligned in the vertical plane with the conduit. In one embodiment, the outlet is defined and surrounded by an angled cover, which serves to deflect the bubbles in the liquid away from the outlet. Preferably, the angle of the cover with respect to the outlet is between 30 and 60°, more preferably between 40 and 50°, and most preferably about 45°. As a result, any rising bubbles will tend to be deflected away from the opening, rather than through it.

The outlet comprises an opening and, for cleaning and draining purposes, it is desirable to provide the opening at the lowest point of the bubble excluder device. In the absence of the opening being provided at the lowest point of the bubble excluder device, fluid may become trapped in the device which may result in contamination.

To reduce or prevent the introduction of bubbles into the probe, it is desirable for the opening of the outlet to be small. However, the smaller the opening, the greater the resistance to flow through the bubble excluder device and probe combination. It is desirable to attain a reasonable rate of flow of liquid medium through the excluder device/probe combination, so that the probe is in contact with regularly changing medium, representative of the culture as a whole outside the bubble excluder device. Typically, the opening of the outlet is circular and has a radius of between 0.5 and 1.5 mm, more preferably between 0.8 and 1.2 mm, and most preferably about 1 mm. This provides a cross-sectional area of around 0.80-7.07 $mm^2$, preferably around 2.01-4.43 $mm^2$, most preferably about 3.14 $mm^2$. Other shaped openings of equivalent cross-sectional area may be provided.

In one embodiment, the outlet comprises a cylindrical tube below the sampling aperture of the probe. Desirably, the length of the tube is kept to a minimum, thus minimising resistance to flow through the bubble excluder device. Preferably, the tube has a length of between 1 and 2 mm, more preferably between 1.2 and 1.8 mm, and most preferably about 1.4 mm, and is wider in cross-section than the opening of the outlet, so as to minimise resistance to flow.

It is desirable that liquid flow through the bubble excluder device should preferably only be via the conduit and the outlet positioned above and below the sampling aperture, respectfully. Thus, in one embodiment, a seal is provided on both sides of the sampling aperture between the probe and the sleeve of the bubble excluder, such that liquid and gas bubbles cannot enter by this route. Preferably, the fluid tight seal is provided by means of a silicone or rubber O-ring at either side of the sampling aperture. Around the sampling aperture, between the O-rings, there must be sufficient space for liquid to flow, with minimal frictional losses.

In one embodiment, a space is provided between the first baffle within the conduit and the sleeve. This has the advantage of allowing the gas bubbles entering the conduit to gain upward velocity before encountering the baffles.

Conventionally, fermenters may be produced comprising means for the inclusion of an optical probe. Normally this takes the form of a bore or aperture provided through the wall of the fermenter. However, the dimensions of the bubble excluder/probe combination of the present invention are typically too great to permit passage of the combination through such a bore or aperture. Conveniently therefore, the bubble excluder device is attached to the probe after insertion of the probe into the fermenter. Alternatively, the sleeve of the bubble excluder device may be attached to the probe prior to insertion into the fermenter, and the conduit attached subsequently. In some embodiments, the inlet means is attached to the probe after insertion of the probe into the fermenter.

In some embodiments, the aperture or bore permitting insertion of a bubble excluder device/probe combination into the fermenter is generally horizontal, such that a conduit and/or outlet attached to a probe in a perpendicular fashion will be substantially vertical and in the optimal orientation to allow egress of gas bubbles from the bubble excluder. However, it is also known to make fermenters with an aperture or bore to accommodate a probe, wherein the aperture or bore is not horizontal but is at an oblique angle to the wall of the fermenter and, typically, sloping downward. In order for the bubble excluder device/probe combination of the present invention to be optimised for use with such a fermenter, the conduit and outlet should ideally be provided at an angle to the axis of the probe, so that when the bubble excluder device/probe combination is in situ in the fermenter the conduit and outlet are substantially aligned in a vertical plane. Fortunately, there are generally a limited number of standard angles which are employed in fermenters, so a corresponding limited range of probe/conduit/outlet combinations can be made which should provide a probe/conduit/outlet combination suitable for use with any fermenter. Alternatively, it should be possible to make a bubble excluder device/probe combination comprising a conduit and/or outlet which is attachable to the body of the probe in a plurality of orientations, each being at a different angle to the axis of the probe, such that the conduit and outlet can be placed in a substantially vertical orientation regardless of the position of the probe.

Typically, the bubble excluder device/probe combination of the present invention may be used to monitor the growth of mammalian, yeast, fungal, bacterial or insect cells.

In yet another aspect, the invention provides a fermenter vessel comprising a bubble excluder device/probe combination in accordance with the second aspect of the invention defined above. Desirably, the fermenter of the present invention comprises a stirred tank. Preferably, the speed at which the medium within the fermenter is stirred may be adjusted in a manner dependent on the type of cells that are grown. Typically, the stirrer speed is set at between 500 and 800 rpm during growth of yeast cells; 100 to 500 rpm during growth of bacterial cells; and less than 100 rpm during growth of mammalian cells. Higher speeds are required during growth of yeast cells in order to maintain oxygen saturation. In contrast, much lower speeds are used during growth of mammalian cells, as these cells are very sensitive to shear forces.

Advantageously, the present invention is accurate over a range of 0.1 to 20 optical density (OD) units, depending on the size of the light path in the probe.

Advantageously, the present invention provides a bubble excluder device/probe combination for continuous, on-line measurement of the cell density of a culture. This avoids the requirement associated with the prior art wherein aliquots of medium must be removed during growth of the culture in order to test the samples off-line or wherein the sample must be degassed intermittently such that measurement of the optical density is not continuous. Advantageously, the conduit and inlet means continuously excludes gas bubbles from the probe which would otherwise interfere with the accuracy of the optical density measurements. Thus, the bubble excluder device/probe combination of the present invention provides a reliable and accurate measurement of the growth of a culture of cells.

Conveniently, that portion of the bubble excluder device/probe combination of the present invention within the fermenter (subjected to agitation and exposure to high concentrations of micro-organisms) does not comprise moving parts and/or electronic components. This has the advantage that the bubble excluder device/probe combination of the present invention is more robust when compared with other probes known in the art.

In a fourth aspect, the present invention provides a method of monitoring the cell density of a culture during aerobic fermentation, using a bubble excluder device/probe combination in accordance with the second aspect of the invention.

In a fifth aspect, the present invention provides a method of excluding bubbles from a probe, the method comprising the step of attaching a bubble excluder device in operable relationship with a probe in the form of a bubble excluder device/probe combination and using said combination within a liquid medium containing bubbles.

In a sixth aspect, the present invention provides a method of making a bubble excluder device in accordance with the first aspect or a bubble excluder device/probe combination in accordance with the second aspect, the method of making a bubble excluder device comprising the step of coupling a suitable conduit and a suitable outlet to a sleeve, and the method of making a bubble excluder/probe combination comprising the step of coupling a suitable conduit and a suitable outlet in operable relationship to a suitable cell density measuring probe.

For the avoidance of doubt, it is hereby expressly stated that any feature of the invention described herein as "preferable", "convenient", "desirable", "advantageous" or the like may be used in the invention in isolation or in any combination with any other feature or features so described, unless the context dictates otherwise.

The present invention will now be described by way of example and with reference to the accompanying drawings, in which.

EXAMPLE 1

Figure 1:
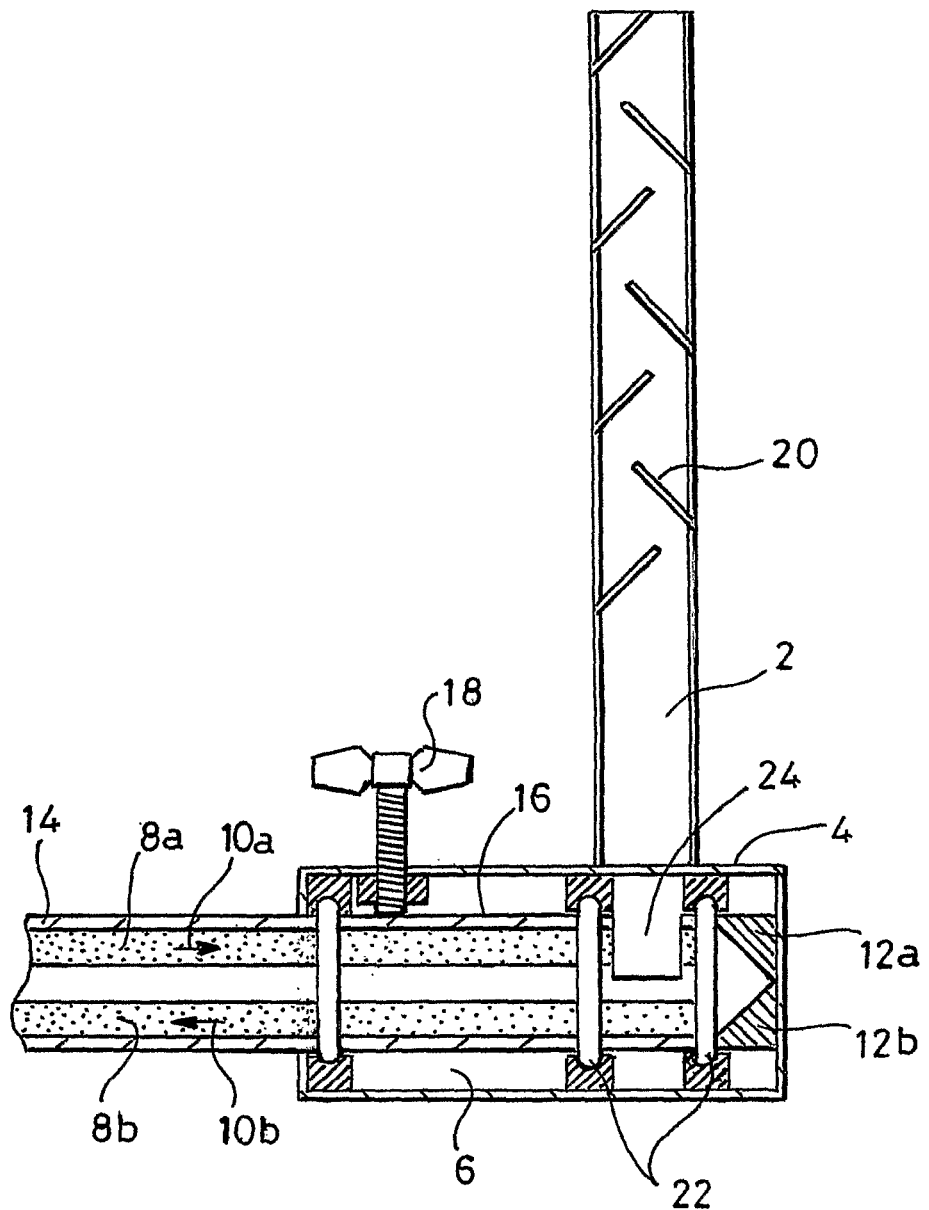
FIGS. 1 and 2 are a schematic representation of some of the components of the bubble excluder device/probe combination for continuous measurement of a culture in accordance with the present invention.
Figure 2:
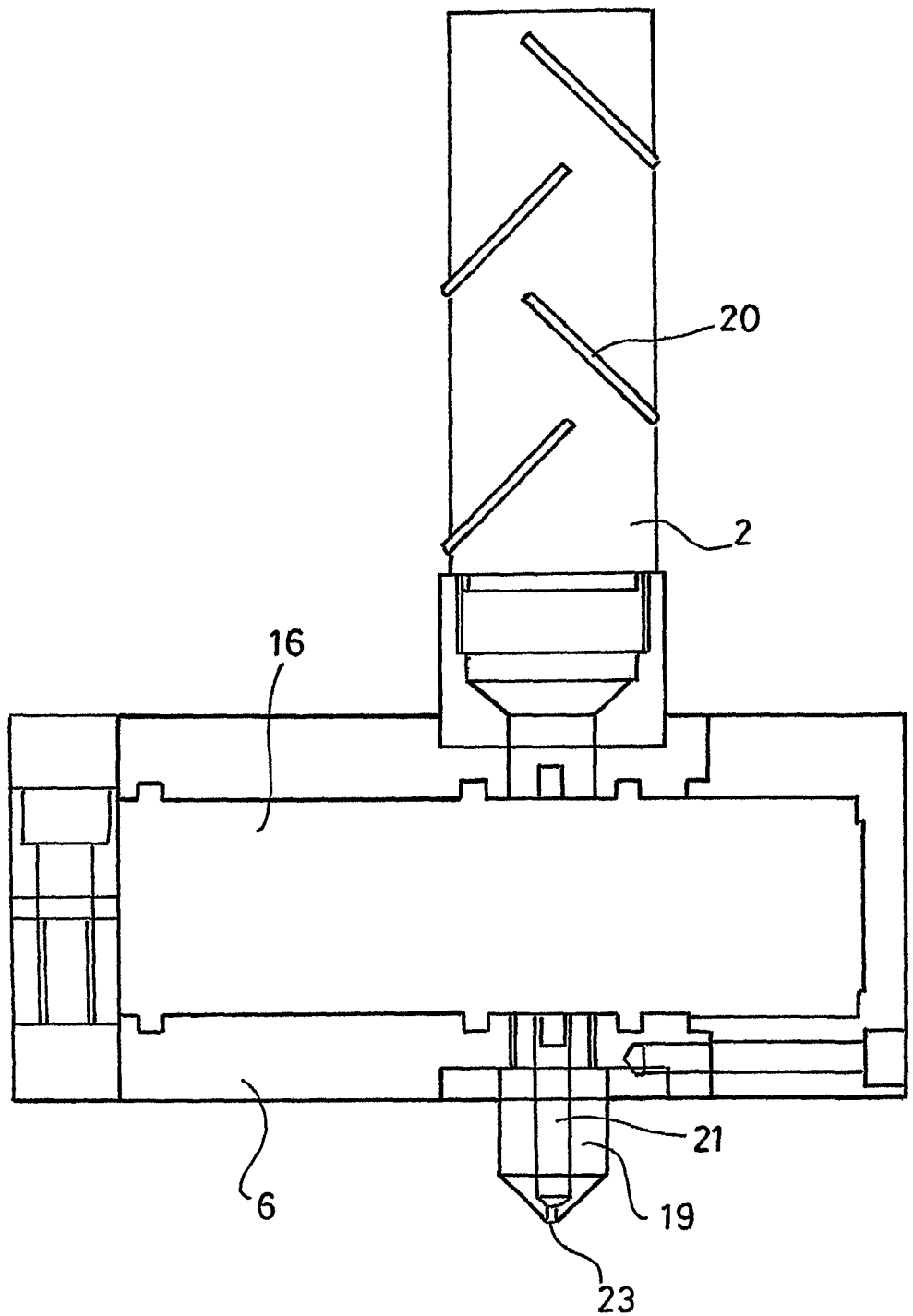

FIGS. 1 and 2 illustrate schematically some of the components of the bubble excluder device/probe combination, in accordance with the preferred embodiment of the invention. In particular, FIG. 1 shows an inlet conduit (2) attached to the outer surface (4) of an optical probe (6). The optical probe (6) comprises two parallel light paths (8a and 8b) which transmit light in opposite directions, as denoted by the arrows (10a and 10b). Two prisms (12a and 12b) are provided at one end of the optical probe (6) and reflect the light such that the direction of the light path (8a) is reversed. A tube or sleeve (14) is provided around the optical fibres (8a and 8b), and the optical probe (6) and prisms (12a and 12b) are secured within a casing (16) which is held in place by a clamp (18). The conduit (2) comprises a plurality of baffles (20) which are positioned at an angle so as to slope in an upward direction. The conduit (2) is attached to the optical probe (6) by means of a fluid tight seal, provided by two rubber O-rings (22), and is positioned in a substantially vertical orientation, generally perpendicular to the axis of the probe.

FIG. 2 shows an outlet (19) attached to the lower surface of the outer region of the optical probe (6). A channel (21) is provided within the outlet (19) and extends from the outer surface of the probe to the bottom of the outlet (19). An opening (23) is provided at the bottom of the outlet (19).

In use, the bubble excluder device/probe combination is positioned within a fermenter, and culture medium is free to enter the sampling aperture (24 in FIG. 1) of the probe via the inlet of the bubble excluder device. The sampling aperture (24) is positioned such that the light path passes through the sample of culture medium. The optical probe (6) is coupled to a spectrophotometer (not shown) which measures the optical density of the culture medium, thus providing a measurement of the concentration of cells within the culture medium. The optical density of the culture medium is measured over a period of time, thus allowing the continuous on-line, measurement of the cell density of a culture.

The inlet conduit (2) is positioned above the sampling aperture (24 in FIG. 1) to allow any gas bubbles in the vicinity of the light path of the optical probe (6) to escape, due to their natural tendency to rise, being less dense than the surrounding medium. The series of baffles (20) provides a pathway for the upward movement of gas bubbles, whilst restricting the undesirable introduction of gas from the culture medium into the sampling aperture. The statistical chance that gas bubbles will enter the sampling aperture decreases with a corresponding increase in the number of baffles present within the conduit (2). In addition, due to the overlapping length of the baffles, there is no straight pathway for the gas bubbles to enter the system. Agitation of the culture medium generates a suction effect across the top of the conduit (2), which promotes replenishment of the culture medium at the sampling aperture (24). Thus, the hydrodynamics of the system are sufficient to replenish the sampling aperture in real time (without significant lag).

Therefore, the conduit and outlet of the bubble excluder serve to prevent or reduce the interaction of bubbles with the probe, thus allowing accurate measurement of the optical density during growth of cells within an aerated fermenter.

EXAMPLE 3

Figure 3A:
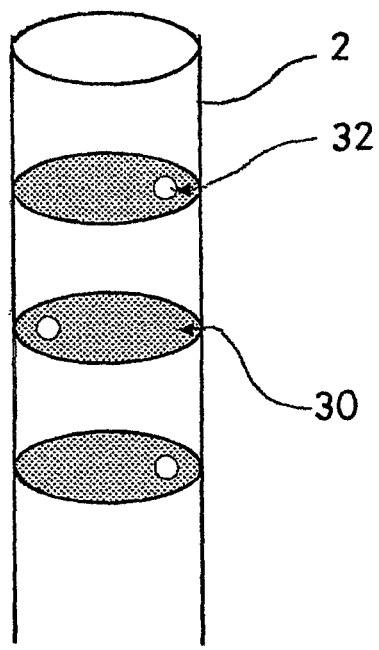
FIGS. 3a and 3b are illustrations of other embodiments of bubble exclusion means that may be present in the bubble excluder device of the invention.
Figure 3B:
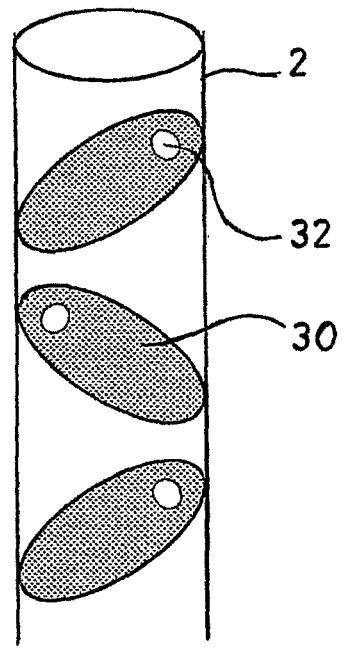

Other embodiments of bubble exclusion means are illustrated in FIGS. 3a and 3b.

In FIG. 3a, a cylindrical inlet conduit (2) is provided with a plurality of perforated metal plates (30) arranged horizontally within the conduit. Each plate (30) is circular, and comprises a single, relatively large perforation (32). The perforations (32) are also circular and of 4-6 mm diameter. The perforations (32) are disposed towards alternate sides of the successive plates (30), thereby establishing a serpentine flow path within the conduit.

The arrangement illustrated in FIG. 3b is essentially similar, except in this embodiment the plates (30) are disposed at an angle. The plates (30) are thus necessarily elliptical in shape. The sloping arrangement of the plates (30) is to be preferred to the horizontal arrangement illustrated in FIG. 3a, since the slope should encourage the upward movement of any buoyant gas bubbles trapped against the underside of the plates (30).

EXAMPLE 4

The growth characteristics of *Saccharomyces cerevisiae* strain WB12 transformed with either plasmid pYES3-Paac2-N6His-aac3 or plasmid pYES3-Paac2-N9His-aac3 were determined in two separate fermentation experiments. In both cases, the same protein was expressed, i.e. a mitochondrial ADP/ATP carrier, but having a different length of histidine tag, comprising either six or nine histidine residues respectively. The precise nature of the strains is of no importance to the invention: the purpose of the example is to illustrate typical results, and the high accuracy, that can be obtained using a bubble excluder device/probe combination in accordance with the invention.

The *S. cerevisiae* cells were grown in media containing the following ingredients and under conditions specified below.

Media: 2 g/l bacterial peptone, 1 g/l yeast extract, 0.2 g/l adenine, 3 g/l glycerol, 20 ml/l ethanol (added after sterilisation), and 2-3 ml antifoam A emulsion, all made up to 1 litre with distilled water.

Fermentation conditions: 30° C., pH5.0, $dO_2$ 80%, agitation 100-800 rpm, and air flowrate 0-15 l/min (0-0.5 vvm).

The agitation and air flow rate were varied using a control loop to maintain $dO_2$ at approximately 80%. In order to control the pH of the medium during fermentation, aliquots of solutions of 5M sodium hydroxide and 10% phosphoric acid were added as necessary.

The fermenter used was a 40 l Applikon ADI 1075 (having a working volume of 30 l) with an ADI 1030 Bio Controller.

The fibre-optic Modular Spectrometer used was a Zeiss MCS500, using Zeiss ASPECT plus software v.1.62, connected to a computer via a PCI interface card. The probe used was a Hellma 661.760-UV Immersion Probe (having a 1 mm optical light path at 660 nm), fitted with a bubble escape conduit essentially as illustrated in FIG. 1, so as to conform with the present invention.

Figure 4:
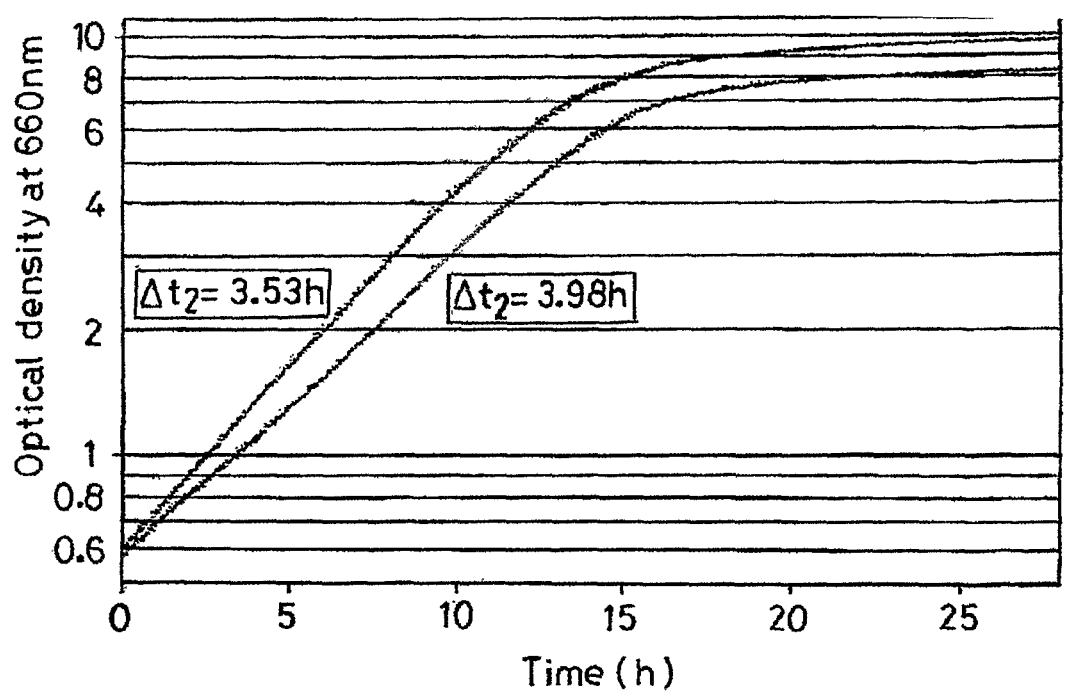
FIG. 4 is a graph showing the growth of S. cerevisiae cells during a fermentation experiment, the growth being continuously monitored by measurement of OD (660 nm) using an optical probe in accordance with the first aspect of the invention.

FIG. 4 shows the growth curves of *S. cerevisiae* WB12 transformed with either plasmid. From the results, it can be seen that the addition of three histidine residues causes a difference in the doubling time, $\Delta t_2$, value observed for the cells. In particular, the cells transformed with pYES3-Paac2-N6His-aac3 had a $\Delta t_2$ value of 3.53 hours, whereas the cells transformed with pYES3-Paac2-N9His-aac3 had a $\Delta t_2$ value of 3.98 hours. This demonstrates the accuracy of the probe of the present invention when assessing the growth of cells in response to the expression of a protein. During fermentation, measurements were taken continuously. However, the values obtained are displayed on the graph at 1 minute intervals.

Figure 5:
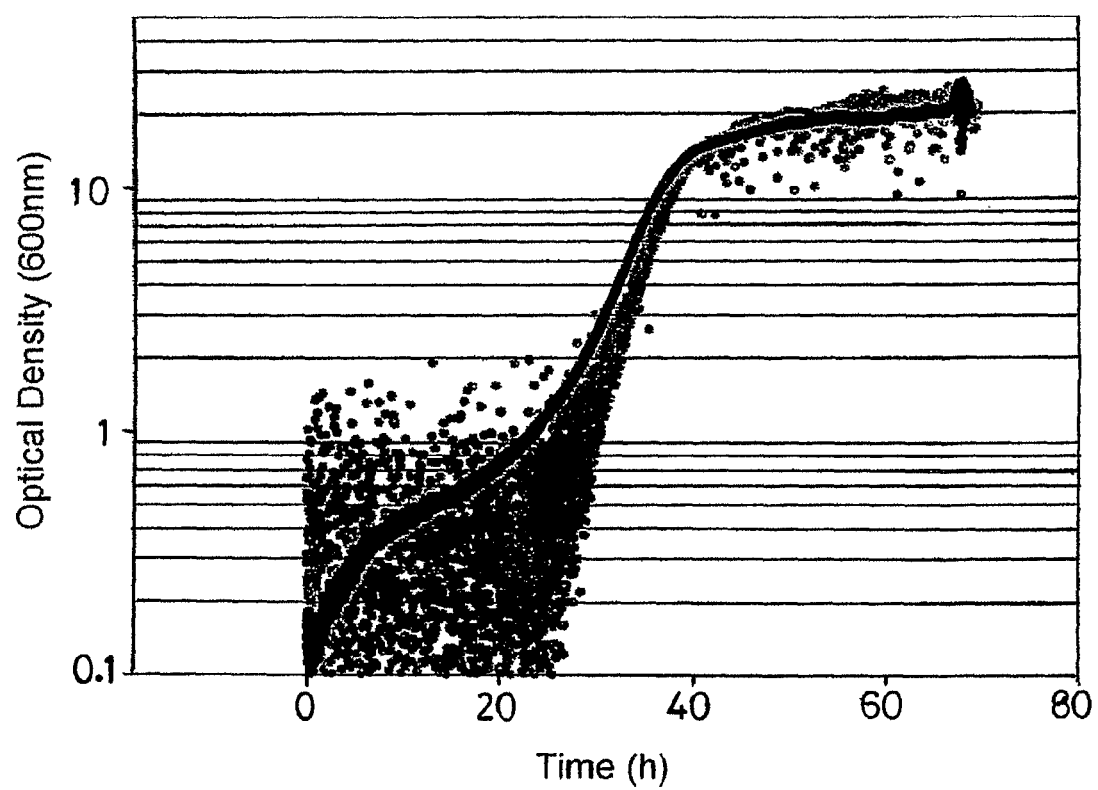
FIGS. 5 and 6 are graphs of OD (600 nm) against time (hours) for two strains of S. cerevisiae during a fermentation experiment.
Figure 6:
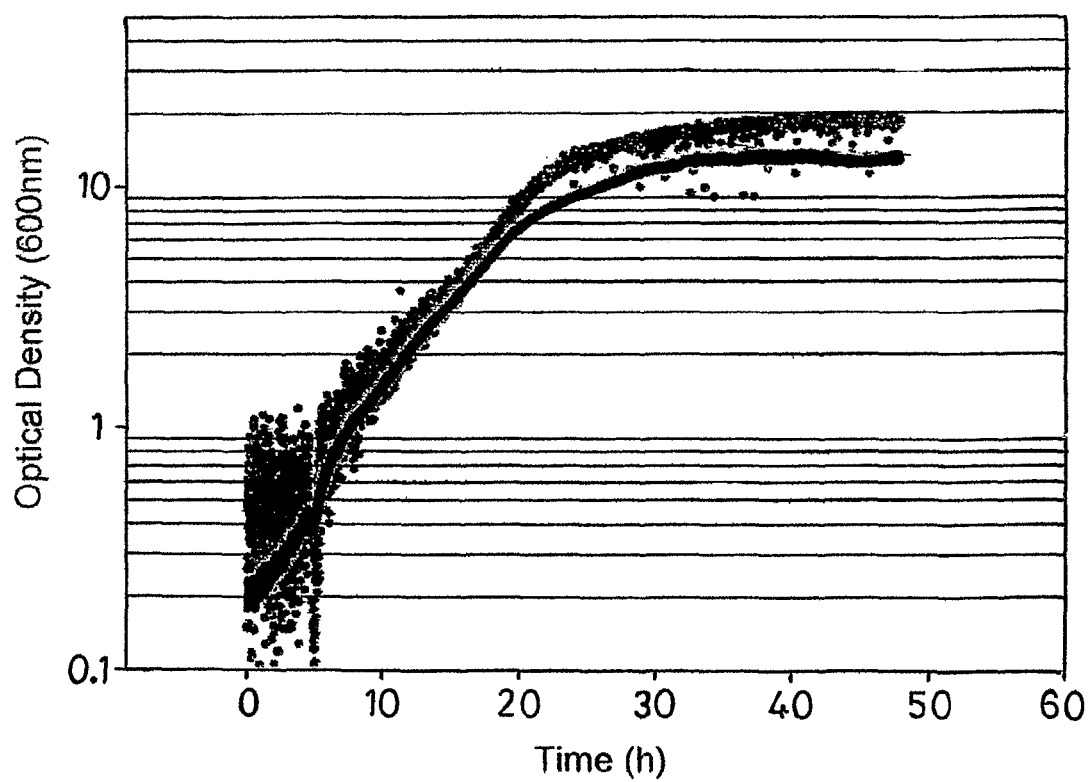

FIGS. 5 and 6 are graphs of Optical Density (at 600 nm) against time (in hours), and show the growth curves of *S. cerevisiae* strain W303 and *S. cerevisiae* strain YHM1 respectively, obtained under similar conditions. Readings were taken using an optical probe fitted with (dark plot) or without (light plot) a bubble excluder device in accordance with the invention. It is readily apparent that use of the bubble excluder device allows far more accurate and reproducible readings of OD, especially within the first 24 hours or so of fermentation.

The invention claimed is:

1. A bubble excluder device adapted for use with, and attachment to, a probe for continuous measurement of the cell density of a culture in a liquid medium in an aerated fermenter, the bubble excluder device comprising an inlet and an outlet to allow flow of liquid through the device, the inlet having a conduit which, in use, is substantially vertical, the conduit comprising means for bubble exclusion which creates a serpentine flowpath within the conduit, the means for bubble exclusion serving to reduce or prevent ingress of bubbles from the liquid medium outside the device.

2. A bubble excluder device according to claim 1, in combination with a probe for continuous measurement of the cell density of a culture, the probe comprising a sampling aperture exposed to the culture within a sleeve of the bubble excluder device to allow the probe to measure a characteristic of the culture.

3. A bubble excluder device/probe combination in accordance with claim 2, wherein the probe measures the optical density of a culture medium.

4. A bubble excluder device/probe combination in accordance with claim 2, further comprising a spectrophotometer.

5. A bubble excluder device/probe combination in accordance with claim 4, wherein the spectrophotometer is an integral component of the probe.

6. A bubble excluder device/probe combination in accordance with claim 4, wherein the spectrophotometer is optically linked to the rest of the probe by means of one or more optical fibres.

7. A bubble excluder device according to claim 1, wherein the means for bubble exclusion is selected from the group consisting of: a plurality of baffles, a plurality of perforated plates, and a channel with a cross-section smaller than the diameter of the majority of bubbles present in the liquid medium.

8. A bubble excluder device in accordance with claim 1, wherein the means for bubble exclusion comprises baffles provided at an angle to the axis of the conduit such that they slope in an upward direction.

9. A bubble excluder device, in accordance with claim 1, wherein the means for bubble exclusion comprises a plurality of baffles, and wherein at least some of the baffles are arranged to overlap, so as to create a sinuous or serpentine fluid flow path between the baffles within the conduit.

10. A bubble excluder device/probe combination in accordance with claim 2, wherein at least one fluid tight seal is provided between the bubble excluder device and an outer surface of the body of the probe.

11. A bubble excluder device/probe combination in accordance with claim 2, wherein a fluid-tight seal is provided at each side of the sampling aperture.

12. A bubble excluder device in accordance with claim 1, wherein the outlet is substantially aligned vertically with the conduit or inlet.

13. A bubble excluder device in accordance with claim 7 in combination with a probe for continuous measurement of the cell density of a culture, the probe comprising a sampling aperture exposed to the culture within a sleeve of the bubble excluder device to allow the probe to measure a characteristic of the culture.

14. A fermenter comprising a bubble excluder device in accordance with claim 1.

15. A fermenter comprising a bubble excluder device/probe combination in accordance with claim 2.

16. A method of monitoring the cell density of a culture during aerobic fermentation, the method comprising use of a bubble excluder device/probe combination in accordance with claim 2.

17. A method of excluding bubbles from a probe in fluid flow contact with a liquid containing bubbles, the method comprising the step of attaching a bubble excluder device in accordance with claim 1 in operable relationship with the probe.

18. A method of making a bubble excluder device in accordance with claim 1, wherein the method comprises the step of coupling a suitable inlet conduit and a suitable outlet to a sleeve.

* * * * *